United States Patent [19]

McAnalley et al.

[11] Patent Number: 5,468,737
[45] Date of Patent: Nov. 21, 1995

[54] WOUND HEALING ACCELERATED BY SYSTEMIC ADMINISTRATION OF POLYSACCHARIDE FROM ALOE

[75] Inventors: Bill H. McAnalley, Grand Prairie; Robert H. Carpenter, Bastrop; Harley R. McDaniel, Grand Prairie, all of Tex.

[73] Assignee: Carrington Laboratories, Inc., Irving, Tex.

[21] Appl. No.: 224,487

[22] Filed: Apr. 7, 1994

Related U.S. Application Data

[63] Continuation-in-part of Ser. No. 136,076, Oct. 13, 1993, which is a continuation-in-part of Ser. No. 864,583, Apr. 7, 1992, Pat. No. 5,308,838, which is a division of Ser. No. 558,905, Jul. 27, 1990, Pat. No. 5,118,673, which is a continuation-in-part of Ser. No. 229,164, Aug. 5, 1988, Pat. No. 5,106,616, which is a continuation-in-part of Ser. No. 144,872, Jan. 14, 1988, Pat. No. 4,851,224, which is a continuation-in-part of Ser. No. 869,261, Jun. 5, 1986, Pat. No. 4,735,935, which is a continuation-in-part of Ser. No. 810,025, Dec. 17, 1985, abandoned, which is a continuation-in-part of Ser. No. 754,859, Jul. 12, 1985, abandoned, which is a continuation-in-part of Ser. No. 750,321, Jun. 28, 1985, abandoned, which is a continuation-in-part of Ser. No. 649,967, Sep. 12, 1984, abandoned, which is a continuation of Ser. No. 375,720, May 7, 1982, abandoned.

[51] Int. Cl.$^6$ .................... A61K 31/715; A61K 45/05
[52] U.S. Cl. .................. 514/54; 514/25; 514/458; 424/74; 424/195.1; 424/423; 424/615; 536/123; 536/124
[58] Field of Search .................... 424/195.1, 72, 424/615, 74, 423; 514/25, 54, 458; 536/123, 124

[56] References Cited

U.S. PATENT DOCUMENTS

| | | | |
|---|---|---|---|
| 4,006,224 | 2/1977 | Prudden | 424/78.06 |
| 4,177,261 | 12/1979 | Dietze et al. | 424/78.06 |
| 4,225,580 | 9/1980 | Rothman et al. | 424/78.06 |
| 4,401,651 | 8/1983 | Knutson | 424/78.06 |
| 4,444,752 | 4/1984 | Prudden | 514/825 |
| 4,456,596 | 6/1984 | Schäfer | 536/5 |
| 4,808,576 | 2/1989 | Schultz et al. | 514/54 |
| 5,106,616 | 4/1992 | McAnalley et al. | 514/54 |

OTHER PUBLICATIONS

"Use of Immunomodulators to Effect Wound Healing in an Aging Animal Model System", Ian Tizard, American Aging Association (AGE) 23rd Annual Meeting, American College of Clinical Gerontology 8th Annual Meeting, Montreal, Quebec, Oct. 1993, Abstract 24.

"The Effect of Acemannan on the Healing of Wounds in Experimental Animals", I. R. Tizard, presented at the International Symposium on Wound Healing and Wound Management, New Orleans, La., Oct. 10–12, 1992.

"Effects of Topical Medications on the Healing of Open Pad Wounds in Dogs", Steven F. Swaim, DVM, MS, et al., Journal of the American Animal Hospital Association, Nov./Dec. 1992, vol. 28, pp. 499–502.

"Accelerated Wound Healing Induced by Macrophage Stimulants in Rats: A Genetically Controlled Phenomenon", Ian R. Tizard, et al., abstract presented at the Join Meeting of the European Tissue Repair Society and Wound Healing Society, Amsterdam, Netherlands, Aug. 22–25, 1993, published in Wound Repair and Regeneration, 1993; 1(2):130.

"Comparison of the Effects of Acemannan on Wound Healing in Young, Old Obese and Old Calorie–Deprived Rats", Ian R. Tizard, et al., presented at the Joint Meeting of the European Tissue Repair Society and Wound Healing Society, Amsterdam, Netherland, Aug. 22–25, 1993, Abstract 102.

"Rapid Acceleration of Wound Healing in Young and Old Rats Induced by Application of a Complex Carbohydrate", Ian R. Tizard, et al., abstract presented at the Keystone Symposia–Progress in Basic Research of Wound Repair and its Application to Clinical Management of Problematic Wounds and Extracellular Matrix in Development and Disease, Silverthorne, Colo., Mar. 29–Apr. 4, 1993, Abstract R321.

*Primary Examiner*—Ronald W. Griffin
*Attorney, Agent, or Firm*—Hitt Chwang & Gaines

[57] ABSTRACT

A method for promoting wound healing involving initiating and accelerating wound repair and tissue regeneration in an animal by systemic administration of a bioactive polysaccharide derived from aloe vera plant.

27 Claims, 2 Drawing Sheets

WOUND HEALING ACCELERATED BY SYSTEMIC ADMINISTRATION OF POLYSACCHARIDE FROM ALOE

REFERENCE TO RELATED APPLICATIONS

The present application is a continuation-in-part of U.S. application Ser. No. 08/136,076, filed, Oct. 13, 1993, and entitled "A Drink Containing Mucilaginous Polysaccharides And Its Preparation," the entire contents and disclosure of which are hereby specifically incorporated by reference. Said U.S. application Ser. No. 08/136,076 is a continuation-in-part of U.S. application Ser. No. 07/864,583, filed Apr. 7, 1992, and entitled "Uses of Aloe Products," the granted on May 3, 1994, as U.S. Pat. No. 5,308,838, entire contents and disclosure of which are hereby specifically incorporated by reference. Said U.S. application Ser. No. 07/864,583 is a divisional application of U.S. application Ser. No. 07/558,905, filed Jul. 27, 1990, and entitled "Uses of Aloe Products," granted on Jun. 2, 1992, as U.S. Pat. No. 5,118,673, the entire contents and disclosure of which are hereby specifically incorporated by reference, corresponds to International Application PCT/US91/08204, filed Nov. 5, 1991, and published under International Publication No. WO 93/08810 on May 13, 1993, the entire contents and disclosure of which are also hereby specifically incorporated by reference. The said U.S. application Ser. No. 07/558,905 is a continuation-in-part of U.S. application Ser. No. 07/229,164, filed Aug. 5, 1988, and entitled "Administration of Acemannan," granted on Apr. 21, 1992, as U.S. Pat. No. 5,106,616. Said U.S. Pat. No. 5,106,616, the entire contents and disclosure of which are hereby specifically incorporated by reference, corresponds to International Application PCT/US89/03381, filed Aug. 3, 1989, and published under International Publication No. WO 90/01253 on Feb. 22, 1990, the entire contents and disclosure of which are also hereby specifically incorporated by reference. The said U.S. application Ser. No. 07/229,164 is a continuation-in-part of U.S. application Ser. No. 07/144,872, filed Jan. 14, 1988, and entitled "Process for Preparation of Aloe Products," granted on Jul. 25, 1989, as U.S. Pat. No. 4,851,224, the entire contents and disclosure of which are hereby specifically incorporated by reference. Said U.S. Pat. No. 4,851,224 is a continuation-in-part of U.S. application Ser. No. 06/869,261, filed on Jun. 5, 1986, and entitled "Processes for Preparation of Aloe Products, Products Produced Thereby and Compositions Thereof," granted on Apr. 5, 1988, as U.S. Pat. No. 4,735,935, the entire contents and disclosure of which are also hereby specifically incorporated by reference. Said U.S. Pat. No. 4,735,935, corresponds to International Application No. PCT/US86/01335, filed Jun. 20, 1986, and published under International Publication No. WO 87/00052 on Jan. 15, 1987, the entire contents and disclosure of which are also hereby specifically incorporated by reference. Said U.S. Pat. No. 4,735,935 is a continuation-in-part of U.S. application Ser. No. 06/810,025, filed Dec. 17, 1985 (now abandoned), which is a continuation-in-part of U.S. application Ser. No. 06/754,859, filed Jul. 12, 1985 (now abandoned) which is a continuation-in-part of U.S. application Ser. No. 06/750,321 filed Jun. 28, 1985 (now abandoned), which is a continuation-in-part of U.S. application Ser. No. 06/649,967 filed Sep. 12, 1984 (now abandoned), which is a continuation of U.S. application Ser. No. 06/375,720 filed May 7, 1982 (now abandoned). Application Ser. No. 06/810,025 is entitled "Processes for Preparation of Aloe Products and Products Produced Thereby." Applications Ser. Nos. 06/754,859; 06/750,321; 06/649,967; and 06/375,720 are entitled "Process for Preparation of Aloe Vera Products."

BACKGROUND

The present invention relates to a method for promoting and accelerating wound healing in an animal by systemic administration of a bioactive polysaccharide derived from an aloe vera plant, more particularly, a method for initiating and accelerating wound repair and tissue regeneration in an animal by systemic administration of a polymeric mannan derivative derived from an aloe vera plant.

I. WOUND MANAGEMENT

Wound healing is a complex series of biochemical and cellular events which result in the contracting, closing and healing of a wound, a traumatic insult to the integrity of a tissue. Wound management must protect the wound from additional trauma and/or environmental factors that would delay the healing process.

Wound management usually consists of a combined systemic and local approach, including the use of antibiotics and the application of a suitable dressing. The principal function of a wound dressing is to provide an optimum healing environment. For example, a wound must be isolated from the external environment before healing can begin. A wound dressing covers the wound mimicking the natural barrier function of the epithelium. To provide an optimum healing environment, a wound dressing should control bleeding, protect the wound from the external environment, prevent further contamination or infection and maintain a moist micro-environment next to the wound surface.

Contamination of a wound may result from contact with an infected object or the ingress of dirt, dust, or microorganism, either at the time of injury or later from the patient's own skin or gastrointestinal tract. For example, it has been found that, unless effective measures are taken to prevent infection, virtually all burns become colonized by bacteria within 12 to 24 hours. In general, infection impedes wound healing by further damaging tissue and promoting inflammation. Subsequent wound repair is delayed by the progression of inflammation consisting of vascular leakage, the release and activation of lytic enzymes, free radical generation, oxygen consumption, and the sensitization of tissue nerve endings. Thus any measure that limits inflammation should promote wound healing provided that it does not compromise the tissue's ability to resist infection or inhibit essential macrophage function.

Up to and including the late 1950's, it was generally accepted that, in order to prevent bacterial infection, a wound should be kept as dry as possible. However, a variety of studies have questioned this philosophy and found that wounds that were kept moist actually healed more rapidly than those that were left exposed to the air or covered with traditional drying dressings. In a review of the properties of occlusive dressings, W. H. Eaglestein, "The Effect of Occlusive Dressings on Collagen Synthesis and Re-epithelialization in Superficial Wounds," *An Environment for Healing: The Role of Occlusion*, Ryan, T. J. (ed.) International Congress and Symposium Series No. 88, London, Royal Society of Medicine, pp. 31–38 (1985) concluded that occlusive dressings that keep wounds moist could increase the rate of epidermal resurfacing by some 40%.

II. AVAILABLE PRODUCTS

As a result of our greater understanding of the wound healing process, many new wound management products have been developed. Each of these products has its benefits and its deficits. In the case of large and/or irregular wounds, the available solid coverings such as gels, plastic, and gelatinous sheets generally do not maintain the close contact required for healing, especially for a wound with an irregular surface. Liquid gels cover the wound surface but are difficult to position and keep in place. In addition, they tend to become less stable at body temperature and flow out of the wound.

A. Absorbent Dressings

Semipermeable and impermeable wound dressings preserve the moisture in a wound but do not actively absorb excess moisture from the wound. The accumulation of wound fluid to the point of flooding can have severe consequences, including skin/tissue maceration and bacterial overgrowth. Dressings that are used to absorb exudate are frequently manufactured from cotton or viscous fibers enclosed in a sleeve of gauze. Such dressings are highly absorbent, but exhibit a tendency to adhere to the surface of the wound as fluid production diminishes. Furthermore, absorbent wound dressings generally do not provide adequate protection for the wound from the outside environment.

B. Nonadherent Dressings

Nonadherent dressings are designed not to stick to the wound. Gauze is often impregnated with paraffin or petroleum jelly to provide a nonadherent dressing. However, the impregnate can wear off, necessitating a dressing change and traumatizing new tissue growth.

In addition to the impregnated gauze type, nonadherent dressings may consist of an absorbent pad faced by a preformed nonadherent film layer.

C. Hydrogel Dressings

Hydrogels are complex lattices in which the dispersion medium is trapped rather like water in a molecular sponge. Available hydrogels are typically insoluble polymers with hydrophilic sites, which interact with aqueous solutions, absorbing and retaining significant volumes of fluid.

Hydrogel dressings are non-adherent and have a higher water content. Hydrogels have been reported to increase epidermal healing. Hydrogels progressively decrease their viscosity as they absorb fluid. In liquefying, hydrogels conform to the shape of the wound and their removal is untraumatic. However, currently available hydrogels are not biodegradable and do not consistently enhance the complete healing process.

D. Absorbable Materials

Absorbable materials are degraded in vivo and do not require removal. Particularly useful internally as hemostats, these materials include collagen, gelatin, and oxidized cellulose.

Gelfoam®, an absorbable gelatin sponge, has been available and used in various surgical procedures as a topical hemostatic agent since the mid 1940's. Gelfoam®, a brand of absorbable gelatin sterile sponge manufactured by Upjohn, is a medical device intended for application to bleeding surfaces as a hemostatic. It is a water insoluble, off-white, non-elastic, porous, pliable product prepared from purified porcine skin collagen. It can absorb and hold within its interstices, many times its weight of blood and other fluids. When not used in excessive amounts, Gelfoam® is absorbed completely, with little tissue reaction. This absorption is dependent on several factors, including the amount used, degree of saturation with blood or other fluids, and the site of use. When placed on soft tissues, Gelfoam® is usually absorbed completely in four to six weeks, without inducing excessive scar tissue.

The *Physician's Desk Reference* (1993 edition) suggests that one use only the minimum amount of Gelfoam® sterile sponge needed to achieve hemostasis, holding it at the site of injury until bleeding stops. Once hemostasis is reached, one should carefully remove any excess Gelfoam® as it may interfere with the healing of skin edges. Furthermore, Gelfoam® must not be placed in intravascular compartments because of the risk of embolization.

In addition, Gelfoam® is not recommended for use in the presence of an infection. If signs of infection or abscess develop where Gelfoam® has been positioned, reoperation may be necessary in order to remove the infected material and allow drainage.

Another precaution is that Gelfoam® should not be used in conjunction with autologous blood salvage circuits as it has been demonstrated that fragments of microfibular collagen pass through the 40 micron transfusion filters of blood scavenging systems.

E. Polysaccharide Dressings

One of the oldest and most enduring materials used in wound management is honey, a complex mixture consisting principally of glucose and fructose. Honey has a low pH, about 3.7, which creates an unfavorable environment for bacterial growth. However, honey has a high osmotic pressure and will effectively draw water out of the surrounding tissue and may dehydrate regenerating epithelial cells.

In recent years, there has also been an increasing interest in the use of sugar, sucrose, as a wound dressing. However, commercial sugar supplies are not always sterile and may contain calcium phosphate, sodium aluminum silicate, or other salts. Although the topical use of sugar appears to be relatively free of adverse effects, sugar has not been shown to be effective as the sole treatment of wounds in controlled clinical tests and may tend to dehydrate epithelial cells, macrophages and fibroblasts.

Available polysaccharide dressings such as Debrisan™, a linear polymer of glucose manufactured by Pharmacia, come formed into beads or granules that are poured into a wound and covered with a simple dressing pad or a semipermeable plastic film. The mobile nature of the beads can make Debrisan™ difficult to use in a shallow wound although the beads do provide a highly absorbent material that is biodegradable.

III. PHARMACOLOGICAL PROPERTIES OF POLYSACCHARIDES

There are many examples in the literature indicating that polysaccharides can exhibit pharmacological and physiological activities without help from other components. Gialdroni-Grassi, *International Archives of Allergy and Applied Immunology*, 76 (Suppl. 1):119–127 (1985); Ohno et al., *Chemical and Pharmaceutical Bulletin*, 33(6):2564–2568 (1985); Leibovici et al., *Chemico-Biological Interactions*, 60:191–200 (1986); Ukai et al., *Chemical and Pharmaceutical Bulletin*, 31:741–744 (1983); Leibovici et al., *Anticancer Research*, 5:553–558 (1985).

One such example relates to development of atherosclerosis. Hyperlipidemia in the general population and especially in familial hypercholesterolemia is associated with coronary heart disease and death. In countries where dietary fiber intake is high, atherosclerosis appears to be uncommon. Trowell et al., Editors, *Refined Carbohydrate Foods*

*and Disease*, London, Academic Press, 207 (1975). Pectin and guar are reported to lower cholesterol in normal and hyperlipidemic patients. Kay et al., *American Journal of Clinical Nutrition*, 30:171–175 (1977). Locust bean gum, a polysaccharide composed of mannose and galactose, decreased the plasma lipoprotein cholesterol concentrations in both normal and familial hypercholesterolemic subjects. Zavoral et al., *American Journal of Clinical Nutrition*, 38:285–294 (1983). Addition of guar gum to carbohydrate meals decreased the postprandial rise of glucose in both normal and diabetic subjects. Jenkins et al., *Lancet*, 2:779–780 (1977). Kuhl, et al., in *Diabetes Care*, 6(2):152–154 (1983) demonstrated that guar gum exhibited glycemic control of pregnant insulin-dependent diabetic patients.

It has been reported that glucan extracted from the yeast *Saccharomyces cervisiae* is a modulator of cellular and humoral immunity. Wooles et al., *Science*, 142:1079–1080 (1963). The extracted glucan also stimulated proliferation of murine pluripotent hematopoietic stem cells, granulocyte macrophage colony-forming cells and cells forming myeloid and erythroid colonies. Pospisil et al., *Experientia*, 38:1232–1234 (1982); Burgaleta, *Cancer Research*, 37:1739–1742 (1977). Maisin et al., [*Radiation Research*, 105:276–281 (1986)] also reported that IV administration of a polysaccharide induced protection of murine hematopoietic stem cells against x-ray exposure, thereby decreasing the mortality of the mice so exposed.

Lackovic et al., [*Proceedings of the Society for Experimental Biology and Medicine*, 134:874–879 (1970)], took yeast cell wall and extracted all constituent matter leaving only "mannans" that he found to be responsible for the induction of an interferon production by peritoneal leukocytes. The "purified mannans" alleged to be responsible for this physiologic response had a molecular weight of 5,500–20,000 Daltons. He theorized that mannans stimulated mouse peritoneal macrophages to produce q-interferon. He also stated that the mannans he isolated showed no toxicity and "they are poor antigens." There was no mention by Lackovic et al. of the use of these "purified mannans" for antiviral activity or for IL-1 stimulation. We submit that Lackovic et al.'s "purified mannans" comprised an assortment of unknown and unidentified substituted and unsubstituted mannans.

Seljelid et al., [*Experimental Cell Research*, 131(1):121–129 (1981)] have observed that insoluble or gel-forming glycans activated macrophages in vitro, whereas the corresponding soluble glycans did not. They postulated that the orientation in which the glycan was presented to the mononuclear phagocyte was decisive for activation. Bogwald, [*Scandinavian Journal of Immunology*, 20:355–360 (1984)] immobilized glycans that had a stimulatory effect on the macrophages in vitro. This led the authors to believe that the spatial arrangements of the glycan was decisive for the effect on the macrophages in vitro. A purified polysaccharide isolated from *Candida albicans* induced an antibody response by human peripheral blood lymphocytes in vitro. Wirz et al., *Clinical Immunology and Immunopathology*, 33:199–209 (1984). Yet there were significant differences between the antiCandida antibodies in sera of normal and Candida-infected individuals. Wirz et al., supra.

As discussed above, the biological activities of polysaccharide materials recovered from plants, yeast and bacteria have demonstrated direct biological activities by eliciting an increase in host defense systems. This reaction is primarily manifested by increased host surveillance for other antigenic substances. Polysaccharides serve as adjuvants (DEAE, Dextran, etc.) and immunomodulators. They also can function as unique T-cell-independent antigens. Both cellular and humoral immunity may be affected, and increased phagocytosis of infectious organisms and tumor cells has been observed, as has enhanced production of immunoglobulins.

The structure of these immunologically active polysaccharides and the types of structural variations appear to be the factors that control their potency and toxicity. Their mode(s) of action remain poorly understood; however, recent evidence indicates that several polysaccharides induce lymphocytes and macrophages to produce a wide range of immunologically active substances. For example, 2-keto-3-deoxy-D-manno-octulosonic acid (KDO) appears to be the chemical portion of lipopolysaccharide (LPS) that provides the minimum signal for macrophage host defense activation [Lebbar et al., *Eur. J. Immunol*, 16(1):87–91 (1986)].

Mannans, including glucomannans and galactomannans, have long been used by man. For example, galactomannans, in the form of plant gums, are widely employed as binders for control of food texture. In addition, some mannans have exhibited significant therapeutic properties [Davis and Lewis, eds. Jeanes, A., Hodge, J., In: American Chemical Society Symposium, Series 15, Washington, DC, American Chemical Society, 1975]. Practitioners of Japanese folk medicine have long believed that extracts of certain fungi have anticancer activity. On investigation, many of these extracts have been found to contain complex carbohydrates with immune-stimulating activity. These carbohydrates are usually polymers of mannose (mannans), glucose (glucans), xylose (hemicellulose), fructose (levans) and mixtures of these. Individual sugars may be bonded in different ways as chains may be branched or unbranched. Glucans have been the most widely studied of these immunostimulatory carbohydrates. It has become increasingly clear that even though they have no toxicity mannans are as effective, if not more effective, than glucans.

IV. PROPERTIES OF ACEMANNAN

A. Purified from Aloe vera

Aloe is a member of the lily family, Harding. *Aloes of the World: A Checklist, Index and Code, Excelsa* 9:57–94 (1979). *Aloe barbadensis* Miller is generally recognized as the "true aloe" because of its wide use and, reportedly, most effective healing power. Although in Japan, *Aloe arborescens* Miller traditionally has been used as a folk remedy for various ailments ranging from gastrointestinal disorders to athlete's foot. Aloe vera is a perennial plant with turgid green leaves joined at the stem in a rosette pattern. The leaves of a mature plant may be more than 25 inches long with sawlike spikes along their margins.

Aloe vera contains two major liquid sources, a yellow latex (exudate) and the clear gel (mucilage). The dried exudate of *Aloe barbadensis* Miller leaves is referred to as aloe. The commercial name is Curacao aloe. It is composed mainly of aloin, aloe-emodin and phenols. Bruce, *South African Medical Journal*, 41:984 (1967); Morrow et al., *Archives of Dermatology*, 116:1064–1065 (1980); Mapp et al., *Planta Medica*, 18:361–365 (1970); Rauwald, *Archives Pharmazie*, 315:477–478 (1982). A number of phenolics, including anthroquinones and their glycosides, are known to be pharmaceutically active. Bruce, *Excelsa*, 5:57–68 (1975); Suga et al., *Cosmetics and Toiletries*, 98:105–108 (1983).

The mucilaginous jelly from the parenchymal cells of the plant is referred to as Aloe vera gel. There are generally no anthroquinones to decompose and cause discoloration of the gel unless the gel is contaminated by an improper processing technique. Aloe vera gel is about 98.5% water by weight. More than 60% of the total solid is made up of polysaccharides of carbohydrate origin. Organic acids and inorganic compounds, especially calcium oxalate, account for the remainder of the solid residue.

Whole leaves, exudates and fresh gels of Aloe plants have been used for a variety of human afflictions. Evidence of their use as a medicinal remedy can be traced to the Egyptians of 400 BC. Aloe vera was also used to embalm the dead, as well as to protect the embalmers from the death-causing agent. Other early civilizations used Aloe vera for skin care, to relieve insect stings and bites, to treat scratches and ulcerated skin, to promote wound healing, to prevent hair loss and as a purgative. Aloe vera was used in the traditional medicine of many cultures as an anthelmintic, cathartic and stomachic and was used inter alia for leprosy, burns and allergic conditions. Cole et al., *Archives of Dermatology and Syphilology*, 47:250 (1943); Chopra et al., *Glossary of Indian Medicinal Plants*, Council of Scientific and Industrial Research, New Delhi (1956); Ship, *Journal of the American Medical Association*, 238(16):1770–1772 (1977); Morton, *Atlas of Medicinal Plants of Middle American Bahmas to Yucatan*, Charles C. Thomas Publisher, 78–80 (1981); Diez-Martinez, La Zabila, *Communicado NO. 46 Sobre Recursos Bioticos Potenciales del Pais*, INIREB, Mexico (1981); Dastur, *Medicinal Plants of India and Pakistan*, D.B. Taraporevala Sons & Co., Private Ltd., Bombay 16–17 (1962).

Depending on the way the leaves are processed, mucilage and sugars are the major components of the dehydrated gel. The sugars found are galactose, glucose, mannose, rhamnose, xylose and uronic acids. Although reports conflict, the mucilage is mainly composed of mannan or glucomannan. Eberendu et al., *The Chemical Characterization of Carrisyn®* (in preparation); Mandal et al., *Carbohydrate Research*, 86:247–257 (1980b); Roboz et al., *Journal of the American Chemical Society*, 70:3248–3249 (1948); Gowda et al., *Carbohydrate Research*, 72:201–205 (1979); Segal et al., *Lloydia*, 31:423 (1968).

For a long time, the controversy over the identity of the active substance(s) in Aloe vera was not settled. It is therefore important to clearly distinguish between the components present in the gel and those found in the exudates. A majority of the gel is a mucilage of mainly polysaccharide nature with minor amounts of various other compounds. It has been observed that in some of the activities there may be some synergistic action between the polysaccharide base and other components. Leung, *Excelsa*, 8:65–68 (1978); Henry, *Cosmetics and Toiletries*, 94:42–43, 46, 48, 50 (1979). For example, several workers report that the effective components for wound healing may be tannic acid [Freytag, *Pharmazie*, 9:705 (1954)] and a kind of polysaccharide. Wound-healing compositions from Aloe arborescens extracts. Kameyama, Japanese Patent #7856995, (1979). Mackee, supra, noted that the gel, not the rind or the exudate, was responsible for the beneficial effects in the treatment of radiation burns, and he stressed the importance of using fresh leaves for effective treatment. Polysaccharides degrade with time, and certain molecular weight sizes may be necessary to elicit a specified pharmacological response. Goto, et al., *Gann*, 63:371–374 (1972).

Literature which reports that polysaccharides possess pharmacological and physiological activities continues to flood the pages of well-respected scientific journals. It is therefore logical that the mucilaginous gel of the Aloe vera plant, which is essentially a polysaccharide, holds the secret to Aloe vera's medicinal properties. The controversy over whether the polysaccharide is a glucomannan, mannan, pectin, or of some other composition, is resolved by a series of chemical purification steps. Yagi et al., [*Planta Medica*, 31(1):17–20 (1977)], using a slightly modified extraction method, isolated acetylated mannan (aloe mannan) from *Aloe arborescens* Miller var *natalensis*. Ovodova [*Khim, Prior. Soedin*, 11(1):325–331 (1975)], however, earlier isolated pectin as the main component of the same aloe species.

B. Chemical Properties of Acemannan

Carrisyn® powder is the brand name given by the assignee of the instant invention to the purified ethyl alcohol extract of the inner gel of the leaves of Aloe barbadensis Miller. The active component of Carrisyn® powder has been designated "acemannan" by the United States Adopted Name Council. Not less than 73% of Carrisyn® extract is acemannan: Carrisyn® extract comprises generally about 73% to 90% acemannan. Carrisyn® extract is generally produced by removing the outer sheath of the leaf, then removing and processing the inner filet or mucilage as follows: pH adjustment, ethanol extraction, freeze drying and grinding. See U.S. application Ser. No. 144,872 filed January 1988 (now U.S. Pat. No. 4,851,224), a continuation-in-part of U.S. application Ser. No. 869,261 (now U.S. Pat. No. 4,735,935), the disclosures of all of which are incorporated herein by reference. Processing in this manner predicts that essentially no covalent bonds are altered and therefore no toxic compounds or byproducts are created. These manufacturing steps were developed to overcome the inability of traditional aloe product producers to standardize and stabilize the polysaccharides.

Acemannan is a fluffy, white, amorphous slightly hygroscopic powder, which is poorly soluble in water and dimethyl sulfoxide and insoluble in most other organic solvents. This powder consists of linear b(1-4)-D-mannosyl units. The polysaccharide is a long chain polymer interspersed randomly with acetyl groups linked to the polymer through an oxygen atom. The generic name for the polymer is acemannan. The degree of acetylation is approximately 0.91 acetyl groups per monomer as determined by the alkaline hydroxamate method. See Hestrin, Journal of Biological Chemistry, 180:240–261 (1949). Neutral sugars linkage analysis indicates that attached to the chain, probably through an a(1-6) linkage, is a D-galactopyranose in the ratio of approximately one for every 70 sugars. The 20:1 ratio of mannose to galactose indicates that galactose units are also linked together, primarily by a b(1-4) glycosidic bond. The chemical structure of acemannan may be represented as follows:

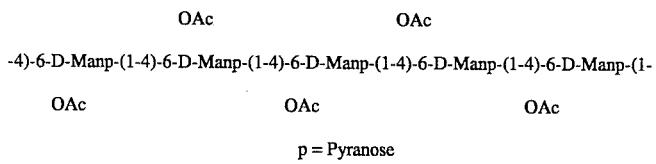

p = Pyranose

C. Toxicology

The toxicological effects of acemannan have been studied in both in vivo and in vitro systems. Acemannan is not mutagenic or blastogenic in in vitro test systems. In vitro, the compound showed no detectable toxicity for H-9, MT-2 and CEM-SS lymphoid cells. In vivo toxicology studies on acemannan include a 91-day subchronic oral toxicity study in dogs, a 180-day chronic oral toxicity study in rats and a 180-day clinical trials in humans. In these studies, no toxic effects were noted in dogs receiving up to 825 mg/kg of acemannan per day for 91 days. No clinical, gross pathologic or toxic effects were noted in rats receiving up to 38.475 ppm acemannan in their feed for 180 days. No adverse clinical or toxic effects were noted in human patients receiving 800 mg per day of acemannan for 180 days in clinical trials.

In pilot studies, administration of acemannan to dogs caused an absolute monocytosis in blood samples taken for complete white blood cell counts and morphology differential. Within 2 hours after oral administration of high doses of acemannan, large activated monocytes appeared in circulation. A similar effect has been observed in humans.

A study was performed using human peripheral blood monocyte cell cultures and $^{14}C$-labeled acemannan to track the incorporation or absorption of acemannan into a biological system. In this study, detectable amounts of $^{14}C$-labeled acemannan were absorbed or ingested by human peripheral monocyte/macrophage cells. Peak incorporation occurred at 48 hours. At a concentration of 5 mg/ml, the $^{14}C$-labeled acemannan was not cytotoxic to the monocyte/macrophage cells, and the weight/volume (w/v) digested cell mass was 760 times greater than the w/v of the digested acemannan solution. These results suggest that the macrophage is capable of maintaining intracellular concentration of acemannan at very high levels that are not cytotoxic.

A pyrogen assay was performed in rabbits in accordance with the pyrogen test protocol outlined in the U.S.P. XXI. Biological Test [151] using a 1 mg/ml injectable solution of acemannan. More frequent temperature measurements were taken than specified in the U.S.P. because of the unknown systemic effects of injected acemannan. Temperature changes in test animals did not exceed minimum changes allowed by the U.S.P. protocol; therefore, the solution met the U.S.P. requirements for absence of pyrogens. Injected acemannan elicited a maximum body temperature increase of 0.30° C. in one rabbit. This temperature rise occurred 90 minutes after injection. Acemannan is an inducer of IL-1 secretion by macrophages and monocytes in vitro. Since IL-1 is a potent pyrogen, this might explain the minimal, delayed temperature rise in this rabbit.

Twenty-four human subjects enrolled in and completed the study of the safety and tolerance of orally-administered acemannan. Clinical laboratory results showed that shifts out of the normal range occurred in the following: $CO_2$ in seven subjects, cholesterol in three subjects, triglycerides in two subjects, phosphorous in one, hemoglobin in four, basophils in two, monocytes in three, eosinophils in three, lymphocytes in four, neutrophils in two, and one each in red and white blood cells. Small numbers of red and white blood cells were also found in the urine. None of these shifts was clinically relevant.

Immune profile results showed group differences between Day 1 to Day 7 values for the following: CD-16, CD-4 (T-4), CD-8--Leu7, CD-4--CD-25, CD-8--CD-16, Leu7 and TQ-1. Mitogen responses were in the low range.

Vital signs did not appear to exceed normal ranges. There were no group differences in urine output. One subject in Group IV had diarrhea and loose stools during the study. One subject in Group I had loose stools during days 2 to 4 of the study. A total of 5 subjects reported a total of eight adverse events. All the events occurred in subjects receiving 1600 or 3200 mg oral acemannan daily for 6 days.

D. Pharmacological Properties of Acemannan

Aloe vera has enjoyed a long history of lay acceptance as possessing "curative" or "healing" qualities. Over the last few years, numerous books and articles meeting scientific standards have been written on Aloe vera. Organizations such as the International Aloe Vera Science Council and recognized medical institutions, through publications and case histories of physicians, veterinarians and other scientists, have given credence to the "aloe phenomenon." Aloe vera has been featured extensively in the field of dermatology, especially for treating radiation-caused skin conditions. Mackee, *X-rays and Radium in the Treatment of Diseases of the Skin*, 3rd Ed., Lea and Febiger, Philadelphia, 319–320 (1938); Rovatti et al., *Industrial Medicine and Surgery*, 28:364–368 (1959); Zawahry et al., *Quotations From Medical Journals and Aloe Research*, Ed. Max B. Skousen, Aloe Vera Research Institute, Cypress, Calif., 18–23 (1977); Cera et al., *Journal of the American Animal Hospital Association*, 18:633–638 (1982). The body of scientific literature documenting medical applications in digestive problems, as a virucidal, bactericidal and fungicidal agent and in gynecological conditions is extensive and has been adequately reviewed by Grindley et al., [*Journal of Ethnopharmacology*, 16:117–151 (1986)].

A number of pharmacology studies have been conducted on Aloe vera gel in recent times. Results have included more rapid healing of radiation burns [Rowe, *J. Am Pharm. Assoc.*, 29:348–350 (1940)] and accelerated healing of wounds [Lushbaugh et al., *Cancer*, 6:690–698 (1953)]. Thermal burns treated with Aloe vera gel heal much faster than untreated burns [Ashley et al., *Plast. Reconstr. Surg.*, 20:383–396 (1957). Rovatto, supra. Rodriguez-Bigas et al., *J. Plast. Reconstr. Surg.*, 81:386–389 (1988)]. The gel is useful in treating leg ulcers [El Zawahry et al., *Int. J. Dermatol*, 12:68–73 (1973)] and in hastening post surgical healing (Payne, Thesis submitted to Faculty of Baylor University, Waco, Tex., MS Degree). Experimental evidence suggests that extracts of Aloe vera have anti-infectious properties [Solar, *Arch. Inst. Pasteur Madagascar*, 47:9–39 (1979)] and enhance phagocytosis [Stepanova, *Fiziol, Akt. Veshchestva*, 9:94–97 (1977)].

Acemannan has also been shown to be a potent stimulator of the immune system. Acemannan induces the production of Interleukin 1 (Ii-1) and prostaglandin $E_2$ ($PGE_2$) in human peripheral blood adherent cells in culture. Acemannan has been shown to be effective as an adjuvant and immunoenhancer and can be effectively used to treat cancer, viral disease, and infections. See U.S. Pat. No. 5,106,616 and U.S. Pat. No. 5,118,673 and references cited therein, the disclosures of which are incorporated herein by reference. All of these patents and this patent application are also assigned to Carrington Laboratories, Inc.

Because of the problems of bioavailability of conventional wound-healing agents, because of the relatively short in vivo half-life of most conventional wound-healing agents, because of the adversed immunological effects of most conventional wound-healing agents, because most conventional wound-healing agents may not conjugate to the proper carbohydrates, and because most wound-healing agents cannot be metabolized, the conventional way of treating a wound is to directly and locally apply the wound-healing agent within the wound site itself.

Despite the known therapeutic properties of many polysaccharides, despite the availability of various gels for treating a wound or lesion, there are few methods available to accelerate normal wound healing. In the case of humans, wound healing in healthy young adults is assumed to proceed at maximum rate and any intervention is confined to debridement, suturing and infection control.

Impaired wound healing is a significant problem in health care. Chronic, non healing wounds are a major cause of prolonged morbidity in the aged human population. This is especially the case in bedridden or diabetic patients who develop severe, non-healing skin ulcers. Thus decubitus ulcers, venous stasis ulcers and diabetic foot ulcers present significant therapeutic problems to physicians and nurses in that they may fail to heal despite competent nursing care. In many of these cases the delay in wound healing is a result of inadequate local blood supply either as a result of continuous pressure or of vascular blockage. As a result, much therapeutic intervention centers on restoring oxygenation to ischemic tissues. This can include the use of occlusive dressings, the use of vascular grafts, or the use of hyperbaric oxygen. Wound care treatments are generally designed to change the physical state of the wound by providing moisture or oxygenation, removing sources of pressure or irritation, or reducing the bacterial load. At the present time there is no treatment directed toward modifying the actual process of wound healing in a positive manner.

Chronic, non-healing wounds in the aged and diabetic population is a wide-spread medical problem. Poor capillary circulation to peripheral tissues due to small artery atherosclerosis or venous stasis are usually at the base of the problem of failure to heal. The tissues which are poorly perfused by blood are often infected with microorganisms that proliferate unchallenged by the innate defense systems of the body that require oxygenated and nourished tissue to function.

In recent years, considerable effort has gone into the study of cytokines and growth factors as molecules that may accelerate wound healing. Some of the most important of these cytokines are fibroblast growth factor, platelet-derived growth factor, and transforming growth factor. While these proteins have shown some success by topical application to decubitus ulcers, there is no evidence that they have a systemic effect. Indeed, given the short biological half-life of these compounds, they are unlikely to survive for long when administered systemically and the possibility that they will have a systemic effect on wound healing is nil. They can also have serious adverse effects when administered systemically.

Thus, there is a need for a method to accelerate normal wound healing in a human by giving a wound-healing agent systemically, which causes wound repair and tissue regeneration.

SUMMARY

It is therefore an object of the present invention to provide a method to promote or accelerate wound healing in an animal.

It is another object of this invention to provide a method to initiate and accelerate wound repair and tissue regeneration in an animal by systemically administering to a human an effective amount of a bioactive polysaccharide, such as acemannan derived from aloe vera plant.

Broadly, one aspect of the present invention pertains to a method of promoting and accelerating healing of a wound in an animal by a systemic administration of an effective amount of a bioactive polysaccharide, derived from aloe vera plant, to the animal. The bioactive polysaccharide can be administered by various systemic routes, before, during or after the wounding, to the animal in a pharmaceutically acceptable carrier.

In one embodiment, acemannan in saline solution is injected parenterally into a patient to promote the healing of wounds in other parts of the body.

In another embodiment, acemannan can be implanted in the form of a solid which is slowly absorbed to cause long term promotion of healing.

In another embodiment, the promotion and acceleration of the healing of a wound in an animal is accomplished by the concurrent use of topical and systemic administration of an effective amount of a bioactive polysaccharide.

In yet another embodiment, the promotion and acceleration of the healing of a wound in an animal is accomplished by implanting a wound healing device into the body of the animal.

In still another embodiment, the bioactive polysaccharide is administered to the animal prior to wound, such as surgery, a method which would result in accelerated healing in the incision.

The foregoing has outlined rather broadly the features and technical advantages of the present invention in order that the detailed description of the invention that follows may be better understood. Additional features and advantages of the invention will be described hereinafter which form the subject of the claims of the invention.

DETAILED DESCRIPTION

Many of the problems discussed above have been solved in the embodiments of the present invention as described below.

The present invention comprises a process of promoting wound healing in an animal by the systemic administration of an effective amount of bioactive polysaccharide, such as acemannan derived from aloe vera plant.

As used herein, the term "bioactive" means "possessing biological activity" such as therapeutic activity which denotes the ability to treat a disease.

The term "systemic" means pertaining to, or affecting, the body as a whole. "Systemic" means acting through the bodily systems after absorption or ingestion of an agent. Thus, systemic relates to the entire organism as distinguished from any of its individual parts.

The term "administration" means given to the animal by oral route, topical application, intraperitoneal injection, intravenous injection, intramuscular injection, subcutaneous injection, solid implant, or other acceptable route of giving a drug or an agent to an animal.

The detailed procedure for isolating the alcohol precipitate of aloe vera extract and acemannan has been described in U.S. Pat. Nos. 4,735,935, 4,851,224, 4,917,890, 4,957,907, 4,959,214, 4,966,892, and 5,106,616, the entire content of both of which is incorporated by reference.

EXAMPLE 1

Systemic Effect of Carrisyn® Powder (55% Acemannan) Monocyte Recruitment By Carrisyn® Powder in Surgical Wounds A protocol entitled *Evaluation of Monocyte Infiltration into a Surgical Wound Treated with Carrisyn® (CSN) Powder* was executed with minipigs to characterize the cellular infiltrate of massive surgical wounds implanted with acemannan-containing CSN powder. The stated purpose was to observe the rate at which monocytic cells infiltrate the area of a surgical wound treated with CSN powder as compared to a saline flushed control wound on the contralateral side of the treated pig and to an untreated wound on a control pig.

Materials & Methods

Figure 1:
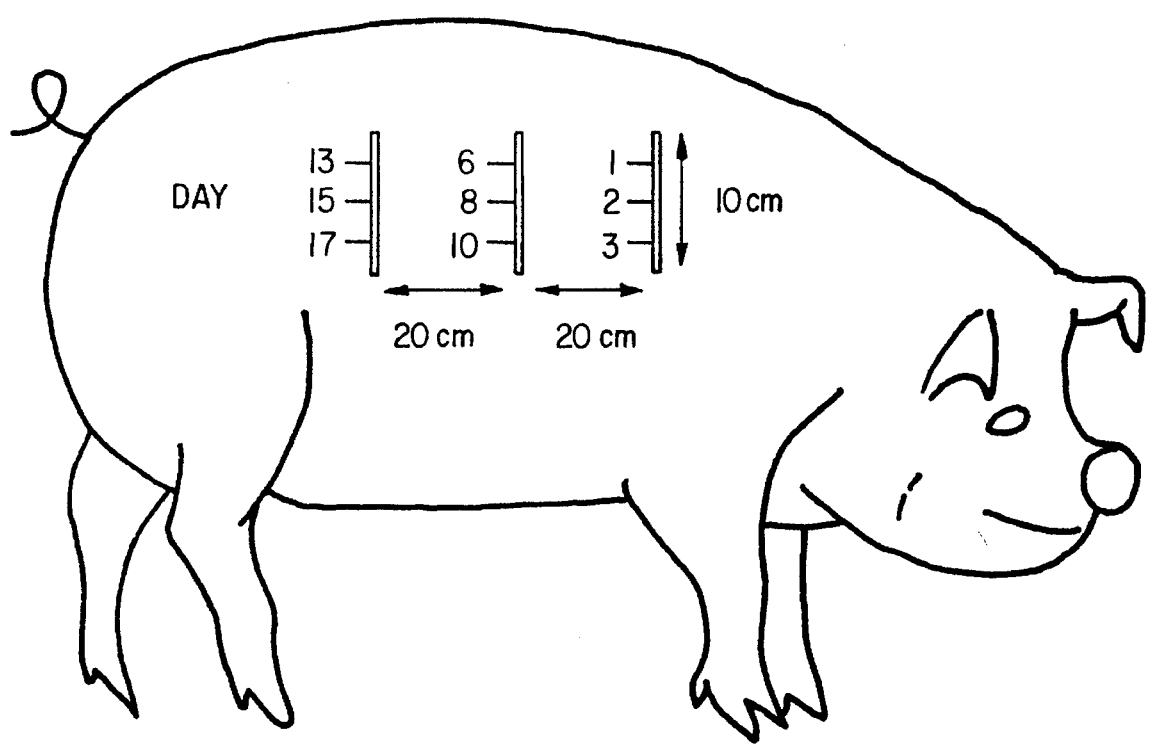
FIG. 1 shows the approximate locations of the implant incisions and biopsy sites on the right-side of the pig. The numbers indicate the day of biopsy after implant. The implant incisions were 10 cm in length and 20 cm apart.
Figure 2:
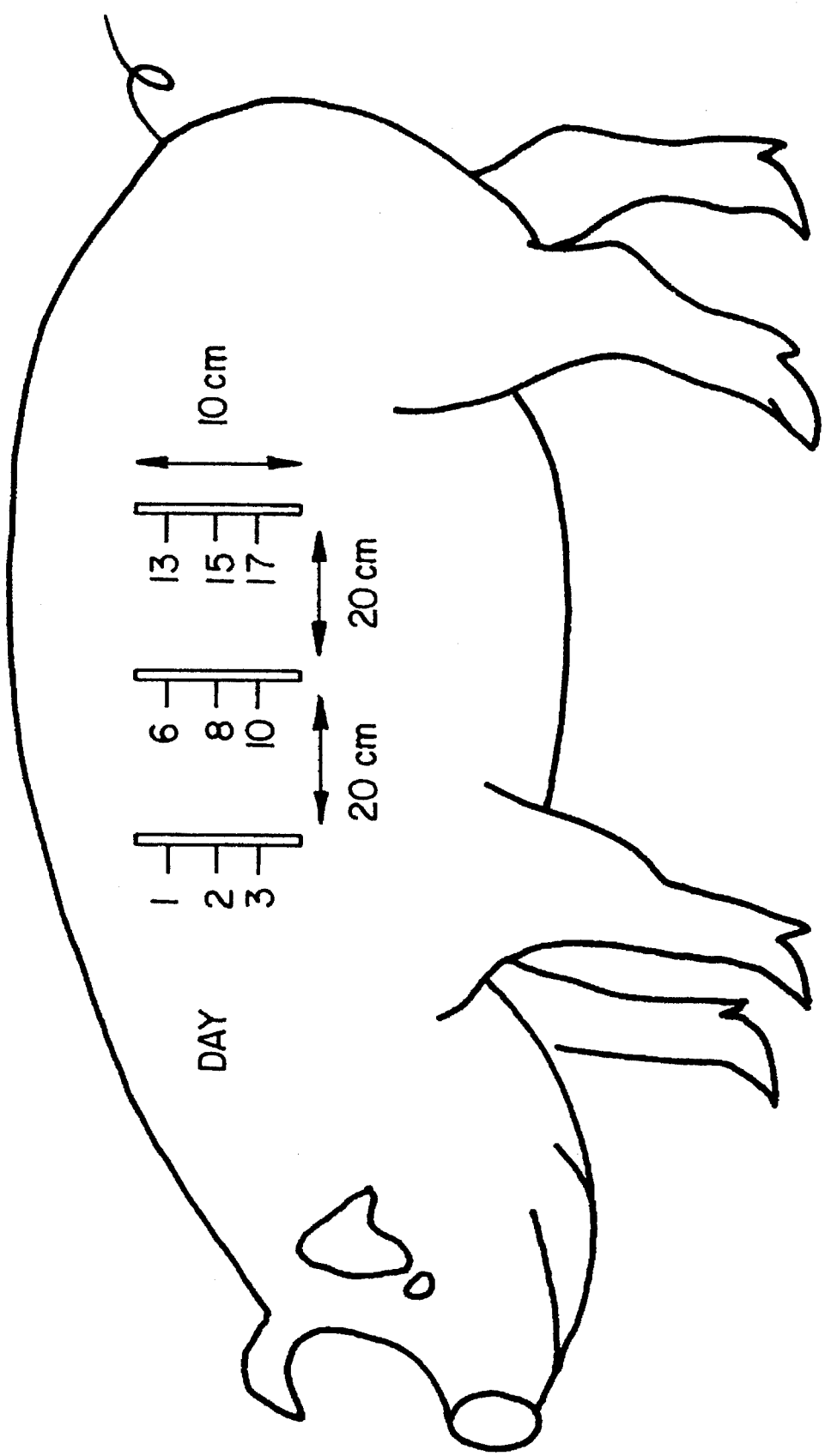
FIG. 2 shows the approximate locations of the implant incisions and biopsy sites on the left-side of the pig. The numbers indicate the day of biopsy after implant. The implant incisions were 10 cm in length and 20 cm apart.

Two 20 to 25 kilogram white male minipigs were selected on the basis of good health, absence of lateral skin abrasions and minimum skin pigment in the experimental surgical areas. The pigs were held for 10 days prior to surgery and two CBC with differentials were performed prior to surgery. On Day 0, three 10 cm full thickness skin incisions were made on each dorsal lateral side of both pigs as shown in FIGS. 1 and 2. The pigs were tranquilized and sedated with ketamine, 10 mg/kg, and the incision sites regionally blocked with lidocaine HCl, Q.S.

A #20 surgical blade was used to make 3 full skin thickness incisions 10 cm long and 20 cm apart. Incisions on the control pig were flushed with 10 cc of sterile normal saline and closed with a single layer of simple interrupted sutures every 2 cm to insure good skin edge apposition. Closure was made with 3/0 monofilament stainless steel wire with a diamond tipped swaged-on needle.

The treated pig's incision treatment consisted of 5 mg/cm of CSN powder placed directly into the wound. This was done by weighing out 50 mg of CSN powder on a sterile paper and evenly distributing the powder along 10 cm of the edge of the paper. The powder was dumped into the wound using the paper as a delivery device. The above standard closure technique was used employing smooth forceps to avoid skin trauma. After one of the three incisions was made, treated and closed, the next incision was made. One side of the treated pig received CSN powder. The contralateral side was saline flushed as with the control pig.

Figure 3:
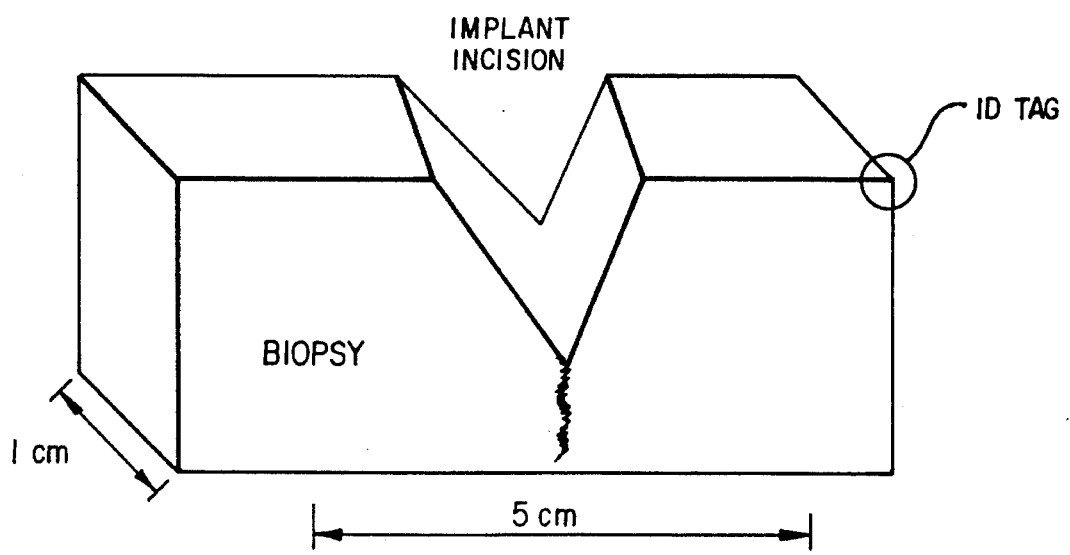
FIG. 3 shows size, positioning, and labeling of the biopsies taken of the implant incisions on various days. The full-skin thickness biopsy size was 5 cm in length and 1 cm in width.

On Day 1, a full thickness biopsy was performed, as shown in FIG. 3, of the treated side and control sides of the pigs. The biopsy was 5 cm long and 1 cm thick. The skin biopsy was placed immediately on a tongue depressor with the ends stapled to the wood to maintain form. This contrivance was then placed in chilled formalin and kept in a refrigerator. The upper right skin edge was identified with a tag and labeled with LP or BP for control or treated, the day number on which the biopsy was performed, and R or L for the side of the pig from which the sample came. This numbered tag was also placed in the formalin bottle. The formalin was changed after 24 hours to assure good fixation. The biopsy area was closed in a routine manner using the same technique as used for the original incisions. Additional biopsies were taken on Days 2, 3, 6, 8, 10, 13, 15, 17.

Histological slides were prepared. Each block was prepared so that the upper right corner of each biopsy sample was visible in the upper right portion of the slide. Slides were labeled as the tissue was labeled; e.g., LP 1 R, on the right edge of the slide. The embedded tissue was cut down until full face sections of tissue could be made. Five consecutive sections were made and mounted. Four slides from the treated and contralateral control side of the treated pig were non-specific esterase stained and one slide H & E stained for review at the sponsor's laboratory. Slides from the control pig were non-specific esterase stained only.

Blood samples were collected and CBC with differential performed on Day 6, Day 13 and Day 17. On Day 17, the pigs were terminated and tissues collected.

Slide interpretation was performed by the sponsor's pathology laboratory consultant. The numbers of monocytic cells were evaluated in the consecutive treated and contralateral control slides with the single slide from the control pig serving as a control.

Results

The results of this experiment included successful completion of multiple biopsies on the pigs throughout the study. Visually, the Carrisyn® Powder treated wounds appeared to initially close at a faster rate than the contralateral side incisions or the control pig incisions. By Day 3, the Carrisyn® powder treated side was well adhered and appeared to be healing slightly faster than the contralateral side, but significantly faster than the control pig. Cellular infiltrate was significantly greater in the treated biopsy than controls.

By the end of the study, the Carrisyn® powder treated side was not healed and exhibited an inflammatory reaction, but was not obviously infected. The original incision and early biopsy sites on the contralateral side of the treated pig had completely healed by Day 17. The control pig's incisions were not healed and were obviously infected.

Necropsy on Day 17 revealed no gross abnormalities in either pig except obvious biopsy site infection in the control pig.

Histopathological examination revealed the presence of small granulomas in the Carrisyn® powder treated incision biopsies. Also present were numerous multinucleated giant cells around some of the Carrisyn® particles still present in the incision site. The contralateral side was normally healed, but also revealed these giant cells without the presence of Carrisyn® particles. The control pig's incisions did not heal and there were few giant cells present in the tissue at the location of the incisions. The pathologist concluded that treatment of the incisions on the treated side of the pig accelerated the healing rate and influenced the cell infiltrate and fibrous connective tissue morphology of the contralateral side. There was greater monocytic infiltrate in the treated incision than the contralateral control. The treated pig's biopsies had a greater monocyte infiltrate than the control pig's.

The treated pig made more progress toward healing than the control pig. There was no histopathological evidence of infection in the Carrisyn® Powder treated pig while the control pig showed evidence of a low grade incision infection. Both pigs showed increases in white cell blood counts; however, the control pig had a pronounced lymphocytosis while the treated pig showed a marked monocytosis.

In conclusion, the treated incisions exhibited a marked overstimulation of the healing process characterized by an inflammatory process and the presence of multinucleated giant cells. A remarkable observation was the presence of a similar reaction on the contralateral side of the treated pig where multinucleated giant cells in the healing tissue were noted without the inflammatory reaction. Also, the treated pig did not have infected wounds while the control pig's wounds were obviously infected.

The pathologist commented on the organization and volume of collagen in the treated and contralateral side of the treated pig as compared to control. These results indicate that Carrisyn® powder placed in a wound may cause a systemic effect as evidenced by the healing rate of untreated wounds on the treated animal, and by the reduced susceptibility to infection. This observation also reveals that differences between treated and untreated wounds on the same experimental animal would be difficult to demonstrate since this experiment suggests a systemic wound healing effect caused by Carrisyn® powder.

EXAMPLE 2

Systemic Effect of Acemannan Given Intramuscular on the Resolution of a Skin Ulceration in a Lupus Patient A 56 year old patient presented at the clinic with a malodorous, circumferential ulceration of the left leg above the ankle and extending anteriorly approximately 15 cm. below the knee cap. The ulceration had been present to various degrees of expansion and healing for 10 years. In the last year amputation had been recommended by several doctors she had seen. The right leg had started to have a reddish, firm plaque area on the outer skin above the ankle in an area 40×20 cm. This was how the left leg ulceration had started 10 years before. The open wound was cultured and a pure *Pseudomonas aeruginosa* growth was obtained. The multiple, extensive ulcerated lesions were provided with an occlusive dressing and covered with Carrington Dermal Wound Dressing with oral and topical antibiotic indicated for use by sensitivity testing. The wound slowly improved for 18 months.

A review of the patient's records indicated she had been seen and treated in a number of institutions and private physicians. Autoantibody titers and biopsy suggested that the problem was of a lupus type destruction of her cutaneous tissues. During the above topical treatment period ulcers would heal, other skin covered areas would turn bluish, then black and necrose deep into the subcutaneous fat. It was difficult to make consistent progress with healing of her leg. Reports from physicians indicated that they had good responses to systemic lupus and rheumatoid arthritis, autoantibody induced diseases, through use of acemannan. The patient was started on sterile injectable acemannan 5 mg I.M. weekly. After about 2 to 3 weeks of systemic acemannan administration, an accelerated rate of re-epithelialization and lack of new tissue destruction was noted in this patient's response. No new tissue destruction was noted and skin covering the granulation tissue was obviously induced and accelerated by the systemic administration of acemannan.

EXAMPLE 3

Systemic Effect of Acemannan Given IP on the Resolution of a Skin Ulceration in a Diabetic Patient A 72 year old female had been a diabetic for years, taking an oral insulin stimulating agent and monitoring her blood sugars poorly. She had a non-healing ulcer on the base of her right great toe for six years. Several types of treatment, including platelet derived growth factors, had been applied to her wound. Due to her failure to respond, amputation of the great toe was recommended the following week.

At presentation the patient was started on an occlusive wound dressing using clear plastic film and Carrington Dermal Wound Dressing. The ovoid, red, ulcer app. 30×15×3 mm was surrounded by a thick horn-like rim of keratin and keloid tissue. Based on prior experience with CDWD, the lesion would have been expected to heal in 120 to 160 days with only topical treatment. The patient also received injection of 5 mg. acemannan I.M. weekly. At 20 days, the lesion had ceased to ooze exudate on the telfa dressing and was totally epithelialized.

Conclusion

The systemic administration of acemannan stimulates and optimizes the immune response of the patient to repair and regenerate the wounded tissue regardless of the over-riding conditions which may be causing the delayed healing (EXAMPLES 2 and 3). In addition, acemannan administered systemically can cause the resolution of a wound in the presence of a pathologic agent (EXAMPLE 2).

The combination of acemannan applied topically and administered systemically has demonstrated more efficacy than topical use alone (EXAMPLES 1 and 3). This effect is easily explained by the synergism of systemically mobilized cells and cytokines reinforcing the local response to the wound. This systemic mobilization is critical if the local response has been insufficient to result in wound healing. This insufficiency can be a result of many factors such as nutrition, infectious disease, and as in EXAMPLES 2 and 3, autoimmune related disease. It also follows that acemannan administered prior to wounding (e.g. surgery) would result in accelerated surgical incision healing.

What is claimed is:

1. A method of promoting and accelerating healing of a wound in an animal, said method comprising:
    systemically administering to said animal an amount of a bioactive polymeric mannan derivative effective in promoting and accelerating wound healing.
2. The method of claim 1, wherein said bioactive polymeric mannan derivative is derived from an aloe vera plant.
3. The method of claim 2, wherein said bioactive polymeric mannan derivative is acemannan.

4. The method of claim 1, wherein said bioactive polymeric mannan derivative is administered to said animal by a parenteral route.

5. The method of claim 1, wherein said bioactive polymeric mannan derivative is administered to said animal by an intraperitoneal or intramuscular route.

6. The method of claim 1, further comprising the step of concurrently administering said bioactive polymeric mannan derivative topically on said wound.

7. The method of claim 1, wherein said bioactive polymeric mannan derivative is administered before, concurrently or after wounding.

8. A method of promoting and accelerating healing of a wound in a human, said method comprising:

systemically administering to said animal an amount of a bioactive polymeric mannan derivative effective in promoting and accelerating wound healing.

9. The method of claim 8, wherein said bioactive polymeric mannan derivative is derived from an aloe vera plant.

10. The method of claim 9, wherein said bioactive polymeric mannan derivative is acemannan.

11. The method of claim 8, wherein said bioactive polymeric mannan derivative is administered to said human by a parenteral route.

12. The method of claim 8, wherein said bioactive polymeric mannan derivative is administered to said human by an intraperitoneal or intramuscular route.

13. The method of claim 8, further comprising the step of concurrently administering said bioactive polymeric mannan derivative topically on said wound.

14. The method of claim 8, wherein said bioactive polymeric mannan derivative is administered before, concurrently or after wounding.

15. A method of promoting and accelerating healing of a wound in an animal, said method comprising:

implanting a device comprising an amount of bioactive polymeric mannan derivative effective in promoting and accelerating wound healing into the body of said animal.

16. The method of claim 15, wherein said bioactive polymeric mannan derivative is derived from an aloe vera plant.

17. The method of claim 16, wherein said bioactive polymeric mannan derivative is acemannan.

18. The method of claim 15, wherein said device is implanted intraperitoneally, intramuscularly, or subcutaneously.

19. The method of claim 15, further comprising the step of concurrently administering said bioactive polymeric mannan derivative topically on said wound.

20. The method of claim 15, wherein said device is implanted before, concurrently or after wounding.

21. A method of preventing or reducing the probability of having a wound in an animal colonized with pathogenic bacteria, said method comprising:

systemically administering to said animal an amount of a bioactive polymeric mannan derivative effective in preventing or reducing the probability of having said wound in said animal colonized with said pathogenic bacteria.

22. The method of claim 21, wherein said bioactive polymeric mannan derivative is derived from an aloe vera plant.

23. The method of claim 22, wherein said bioactive polymeric mannan derivative is acemannan.

24. The method of claim 21, wherein said bioactive polymeric mannan derivative is administered to said animal by a parenteral route.

25. The method of claim 21, wherein said bioactive polymeric mannan derivative is administered to said animal by an intraperitoneal, intramuscular, or implant route.

26. The method of claim 21, further comprising the step of concurrently administering said bioactive polymeric mannan derivative topically on said wound.

27. The method of claim 21, wherein said bioactive polymeric mannan derivative is administered before, concurrently or after wounding.

* * * * *

UNITED STATES PATENT AND TRADEMARK OFFICE
CERTIFICATE OF CORRECTION

PATENT NO. : 5,468,737
DATED : November 21, 1995
INVENTOR(S) : McAnalley et al.

It is certified that error appears in the above-indentified patent and that said Letters Patent is hereby corrected as shown below:

Col. 1, line 14, following ""Uses of Aloe Products,"", delete "the".

Col. 1, line 15, following "U.S. Pat. No. 5,308,838,", insert -- the --.

Col. 9, in the equation, delete "-4)-6-D-Manp-(1-4)-6-D-Manp-(1-4)-6-D-Manp-(1-4)-6-D-Manp-(1-4)-6-D-Manp-(1-" and insert therefore -- -4)-ß-D-Manp-(1-4)-ß-D-Manp-(1-4)-ß-D-Manp-(1-4)-ß-D-Manp-(1-4)-ß-D-Manp-(1- --.

Col. 11, line 2, delete "(Ii-1)" and insert therefore -- (Il-1) --.

Signed and Sealed this

Twenty-sixth Day of March, 1996

Attest:

BRUCE LEHMAN

*Attesting Officer*         *Commissioner of Patents and Trademarks*